United States Patent [19]
Demers

[11] Patent Number: 6,117,396
[45] Date of Patent: Sep. 12, 2000

[54] DEVICE FOR DELIVERING DEFINED VOLUMES

[75] Inventor: Robert Richard Demers, Middlesex, N.J.

[73] Assignee: Orchid Biocomputer, Inc., Princeton, N.J.

[21] Appl. No.: 09/025,380

[22] Filed: Feb. 18, 1998

[51] Int. Cl.[7] .................................................. G01N 1/14
[52] U.S. Cl. .......................... 422/100; 422/81; 422/103; 436/180; 222/394
[58] Field of Search ............................ 422/63, 68.1, 81, 422/100, 103, 104; 436/43, 174, 179, 180; 222/394, 330

[56] References Cited

U.S. PATENT DOCUMENTS

| | | |
|---|---|---|
| 3,957,583 | 5/1976 | Gibson et al. . |
| 4,038,151 | 7/1977 | Fadler et al. . |
| 4,271,119 | 6/1981 | Columbus . |
| 4,283,262 | 8/1981 | Cormier et al. . |
| 4,310,399 | 1/1982 | Columbus . |
| 4,316,233 | 2/1982 | Chato et al. . |
| 4,426,451 | 1/1984 | Columbus ............................... 436/518 |
| 4,517,338 | 5/1985 | Urdea et al. . |
| 4,601,881 | 7/1986 | Webster . |
| 4,634,057 | 1/1987 | Coffee et al. . |
| 4,676,274 | 6/1987 | Brown . |
| 4,704,256 | 11/1987 | Hood et al. . |
| 4,908,112 | 3/1990 | Pace . |
| 4,911,782 | 3/1990 | Brown . |
| 5,077,017 | 12/1991 | Gorin et al. ............................. 422/100 |
| 5,089,233 | 2/1992 | DeVaney, Jr. et al. . |
| 5,104,813 | 4/1992 | Besemer et al. ......................... 436/179 |
| 5,144,139 | 9/1992 | Hillman et al. . |
| 5,176,881 | 1/1993 | Sepaniak et al. . |
| 5,180,480 | 1/1993 | Manz . |
| 5,197,517 | 3/1993 | Perera . |
| 5,240,578 | 8/1993 | Tatsumi . |
| 5,250,263 | 10/1993 | Manz . |
| 5,252,296 | 10/1993 | Zuckermann et al. . |
| 5,279,791 | 1/1994 | Aldrich et al. . |
| 5,288,468 | 2/1994 | Church et al. . |
| 5,296,375 | 3/1994 | Kricka et al. . |
| 5,310,463 | 5/1994 | Dadoo et al. . |
| 5,378,334 | 1/1995 | Dadoo et al. . |
| 5,417,925 | 5/1995 | Goodale et al. ......................... 422/103 |
| 5,427,946 | 6/1995 | Kricka et al. . |
| 5,443,673 | 8/1995 | Fisher et al. . |
| 5,480,614 | 1/1996 | Kamahori . |
| 5,503,805 | 4/1996 | Sugarman et al. . |
| 5,603,351 | 2/1997 | Cherukuri et al. . |
| 5,627,041 | 5/1997 | Shartle ................................... 435/7.24 |
| 5,646,039 | 7/1997 | Northrup et al. . |
| 5,677,195 | 10/1997 | Winkler et al. ......................... 436/518 |
| 5,681,484 | 10/1997 | Zanzucchi et al. ........................ 216/2 |
| 5,731,212 | 3/1998 | Gavin et al. . |
| 5,772,966 | 6/1998 | Maracas et al. ......................... 422/100 |
| 5,824,204 | 10/1998 | Jerman .................................. 204/601 |
| 5,846,396 | 12/1998 | Zanzucchi et al. ..................... 204/601 |

FOREIGN PATENT DOCUMENTS

| | | |
|---|---|---|
| 0 377 202 A2 | 7/1990 | European Pat. Off. . |
| 0 501 796 A2 | 9/1992 | European Pat. Off. . |
| 0 595 290 A2 | 5/1994 | European Pat. Off. . |
| 0 672 835 A1 | 9/1995 | European Pat. Off. . |
| 92/21883 | 12/1992 | WIPO . |

OTHER PUBLICATIONS

International Search Report, PCT/US97/18266, Our Ref. SAR 12385PCT.

Primary Examiner—Long V. Le
Attorney, Agent, or Firm—Lyon & Artz, PLC

[57] ABSTRACT

Provided is a liquid dispensing device for delivering defined volumes comprising (a) a reagent fill channel, (b) one or more metering capillaries connected to the reagent fill channel and having an exit, and (c) one or more sources of gas connected to the reagent fill channel, wherein after filing the one or more metering capillaries the reagent fill channel can be drained of liquid while liquid is retained in the one or more metering capillaries, and the source of gas can be operated to eject the liquid in the metering capillaries.

18 Claims, 11 Drawing Sheets

FIG.13C

DEVICE FOR DELIVERING DEFINED VOLUMES

The present invention relates to a device for delivering defined volumes, particularly defined small volumes for use in microscaled analytical or synthetic processes.

A number of related applications have been filed on liquid dispensing systems that use electrode-based pumps including U.S. Pat. No. 5,585,069 (Dkt. No. 11402), U.S. Pat. No. 5,593,838 (Dkt. No. 11402A); Ser. No. 08/454,771, filed May 31, 1995 (Dkt. No. 11402B); U.S. Pat. No. 5,643,738 (Dkt. No. 11402C); U.S. Pat. No. 5,681,484 (Dkt. No. 11402D); (application Ser. No. 08/454,772, filed May 31, 1995, now abandoned; U.S. application Ser. No. 08/454,768, filed May 31, 1995 (Dkt. No. 11402F); U.S. Pat. No. 5,846,396 (application Ser. No. 08/556,036, filed May 31, 1995, Dkt. No. 11402G); U.S. Pat. No. 5,632,876 (Dkt. No. 11717); U.S. application Ser. No. 08/556,423, Nov. 9, 1995 (Dkt. No. 11717A); U.S. application Ser. No. 08/645,966, May 10, 1996 (Dkt. No. 11717B); U.S. Pat. No. 5,603,Dkt. No. 11740); and U.S. application Ser. No. 08/744,386, Nov. 7, 1996 (Dkt. No. 12385A). These patents and applications are hereby incorporated herein by reference in their entirety.

The invention addresses the problem of distributing metered volumes of liquids to a multiplicity of micro-scaled sites such as reaction sites. The invention provides an inexpensive device for distributing multiple small volumes.

Systems are being developed that allow for complex chemistries or other mixing processes to be conducted at large number of sites—for example 100, 1,000 or 10,000 sites—in a relatively small device. Some of the applications for such high density devices for relaying liquids do not require precise metering of the liquids dispensed into a particular site. Other applications, however, place a greater premium on precise metering mixing. In many cases, precise metering is only needed in limited parts of the process, while other parts of the process may only need reliable but less precise pumping of liquid. The high precision device of the present invention, in a preferred embodiment, allows a receiving substrate to be attached to inject metered amounts of liquid to defined positions of the receiving substrate. Several reagents can be dispensed in sequence through this device by clearing the used channels by appropriate use of purging gas or vacuum. The receiving substrate can also be transferred to another device where other liquids, which may or may not be metered, can be added to the defined positions.

SUMMARY OF THE INVENTION

In one embodiment, the invention provides a liquid dispensing device for delivering defined volumes of a liquid, the device comprising: (a) a reagent fill channel; (b) one or more metering capillaries connected to the reagent fill channel and having an exit; and (c) one or more sources of gas connected to the reagent fill channel, wherein after filling the metering capillaries the reagent fill channel can be drained of liquid while liquid is retained in the one or more metering capillaries, and the source of gas can be operated to eject the liquid in the one or more metering capillaries. Preferably, the device has two or more said reagent fill channels connected to the one or more metering capillaries, wherein the liquid dispensing device is adapted to dispense via separate reagent fill channels two or more different reagents. Preferably, the device further comprises, in the reagent fill channel, two or more connections to gas sources, where two or more of the gas sources can be connected to separate gas sources. In an embodiment, the device further comprises a controller for sequentially activating the gas sources to sequentially and linearly pressurize segments of the reagent fill channel.

In another embodiment, the invention provides an aliquoting apparatus comprising: (1) a first liquid dispensing device as described in the preceding paragraph and a second liquid dispensing device (which can be distinct from the above described device); and (2) a transfer device (preferably motorized) for moving a receiving substrate from the first liquid dispensing device to the second liquid dispensing device, wherein the receiving substrate receives liquids ejected from the first or second liquid dispensing devices. The second device can be, for example, a liquid distribution device such as is described in U.S. Pat. No. 5,846,396 (application Ser. No. 08/556,036, filed May 31, 1995, Dkt. No. 11402G). Preferably, the aliquoting apparatus having the first and second liquid dispensing devices comprise mechanical, magnetic, electrical or optical alignment markers and the apparatus is adapted to operate with receiving substrates having mechanical magnetic, electrical or optical alignment markers. Preferably, the aliquoting apparatus further comprises an alignment detection device for determining the relationship between the alignment markers on either the first or second liquid dispensing system and the alignment markers on a receiving substrate and producing corresponding alignment data; and a controller for receiving alignment data from the alignment detection device and operating the motorized transfer device to improve the alignment data.

In still another embodiment, the invention provides a method of dispensing two or more liquids into two or more mixing sites on a receiving substrate comprising: (i) providing a first and a second liquid dispensing device of the invention with the receiving substrate aligned with the first liquid dispensing device; (ii) dispensing, from the first liquid dispensing device, a first liquid to the mixing sites; (iii) moving the receiving substrate to align with the second liquid dispensing device; and (iv) dispensing, from the second liquid dispensing device, a second liquid to the mixing sites. In another option, the invention provides a method of dispensing two or more liquids into two or more mixing sites on a receiving substrate comprising: (i) providing a liquid dispensing device of claim 1, with the receiving substrate aligned therewith; (ii) dispensing, from the liquid dispensing device, a first liquid to the two or more mixing sites; (iii) filling one or more reagent fill channels of the liquid distribution device with a second liquid; and (iv) dispensing from the liquid dispensing device the second liquid to the two or more mixing sites.

BRIEF DESCRIPTION OF THE DRAWINGS

FIG. 1A shows a three-dimensional representation of a liquid dispensing device 90A while

DEFINITIONS

The following terms shall have, for the purposes of this application, the meaning set forth below. In particular, for the purpose of interpreting the claims, the term definitions shall control over any assertion of a contrary meaning based on other text found herein:

capillary dimensions

"Capillary dimensions" are dimensions that favor capillary flow of a liquid. Typically, channels of capillary dimensions are no wider than about 1.5 mm. Preferably channels are no wider than about 500 $\mu$m, yet more preferably no wider than about 250 $\mu$m, still more preferably no wider than about 150 $\mu$m.

capillary barrier

A "capillary barrier" is a barrier to fluid flow in a channel comprising an opening of the channel into a larger space designed to favor the formation, by liquid in the channel, of an energy minimizing liquid surface such as a meniscus at the opening.

mesa

A "mesa" is a protrusion on which the entrance or exit of a metering capillary is located. Preferably, the mesa serves to reduce the surface area adjacent to the entrance or exit at which a liquid can be retained by a wetting phenomenon.

metering capillaries

A "metering capillary" is a channel designed to fill to a known amount of liquid, which amount can then be dispensed with gas pressure.

DETAILED DESCRIPTION OF THE INVENTION

Described elsewhere in co-pending patent applications, such as U.S. Pat. No. 5,846,396 (Ser. No. 08/556,036, filed May 31, 1995, Dkt. No. 11402G), and U.S. application Ser. No. 08/744,386, filed Nov. 7, 1996, (Dkt. No. 12385A) are small-scaled liquid dispensing systems that allow the distribution of liquids to a large number of sites, such as 10,000 sites arrayed on a 4×4 inch glass plate. These devices are useful for example in combinatorial synthesis procedures.

The present invention provides additional tools for distributing liquids to small, closely spaced sites.

Figure 1A:
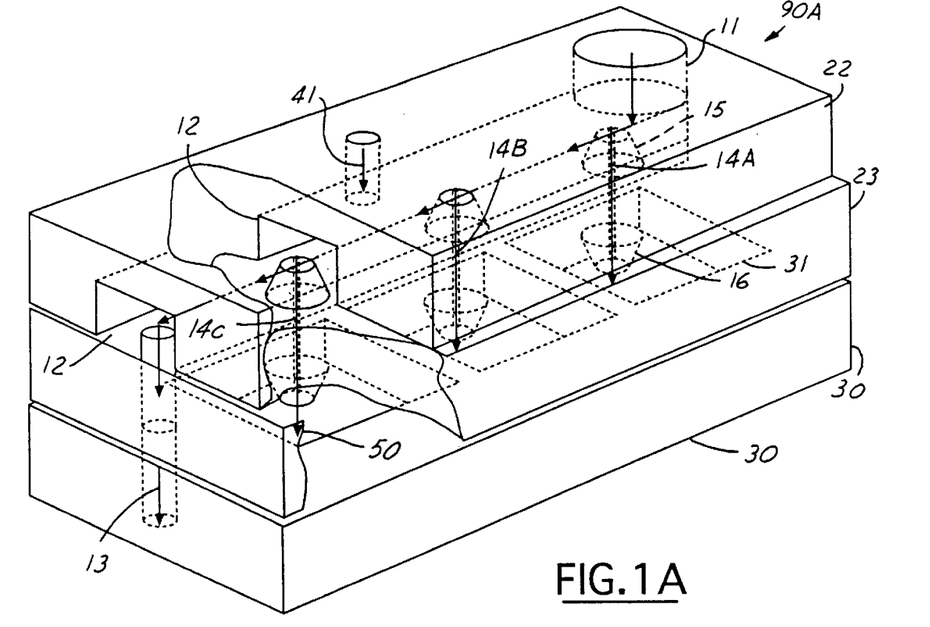
Figure 1B:
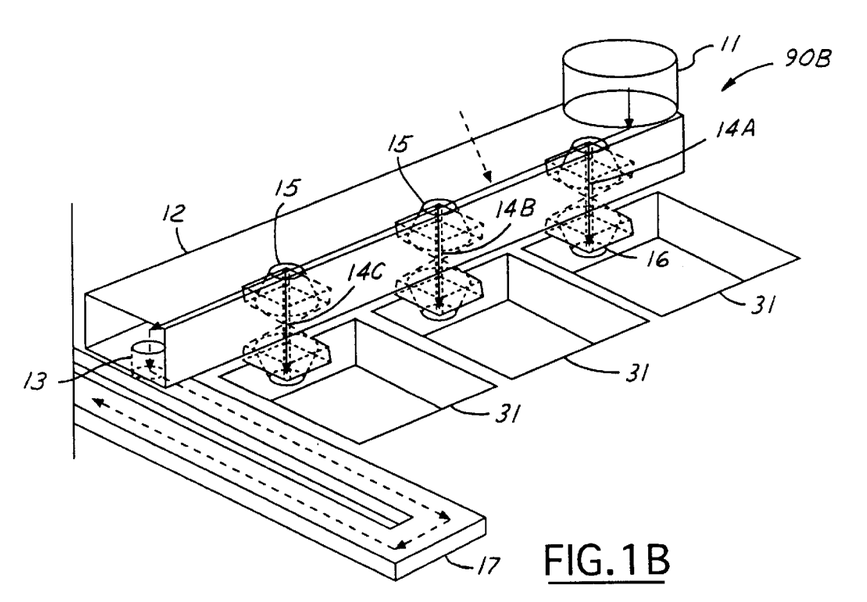
FIG. 1B shows a liquid dispensing device 90B that further includes a reagent sink channel 17.

In FIG. 1A is shown a three-dimensional representation of a liquid dispensing device 90A Solid arrows in the illustration indicate the direction of liquid flow and hollow arrows indicate the direction of gas flow for fluid transfer. Liquid is introduced from a source (not shown) into reagent fill channel 12 through a reagent feed inlet 11. Excess liquid in the reagent fill channels drains through the excess fluid outlet 13. The outlet can connect with a reagent sink channel which can provide a channel of capillary dimensions to enhance capillary flow through the liquid dispensing device 90A. FIG. 1B shows a liquid dispensing device 90B with a reagent sink channel 17. The liquid flow can be the result of capillary flow processes or can be the result of pumping. In flowing through the reagent fill channel 12, liquid enters and fills a series of metering capillaries 14, for example first metering capillary 14A, second metering capillary 14B and third metering capillary 14C. Capillary barriers formed at the exits of the metering capillaries can prevent premature ejection of the liquid from the metering capillaries 14. The dimensions of reagent sink channel can be selected to promote capillary flow through the channel and thereby through reagent fill channel 12, or, in the case where flow into the reagent fill channel is promoted by a pump, the dimensions are selected so that excess pressure is relieved by liquid flow from the reagent fill channel 12 to the excess fluid outlet 13, where such excess pressure might otherwise cause liquid to be ejected from the metering capillaries 14.

Figure 2A:
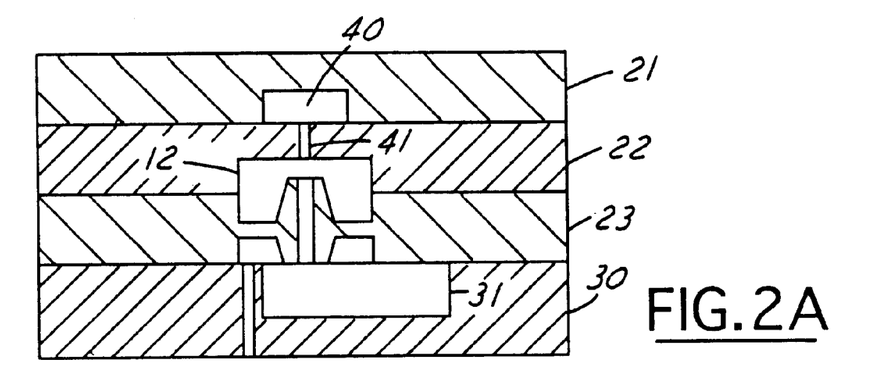
FIGS. 2A, 2B and 2C show cross-sectional representations of the liquid dispensing device 90 at various stages of operation.
Figure 2B:
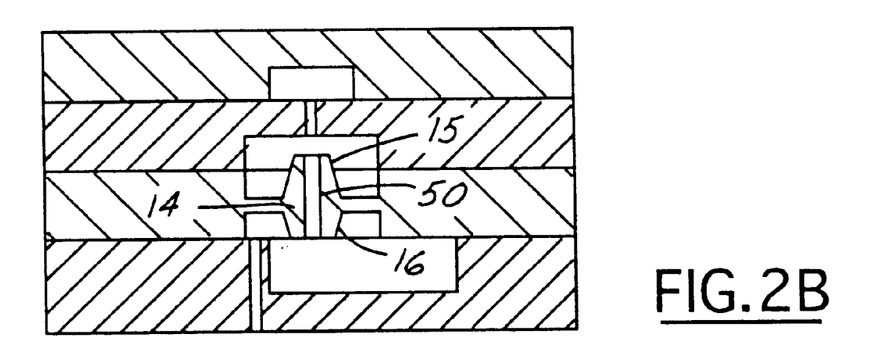
Figure 2C:
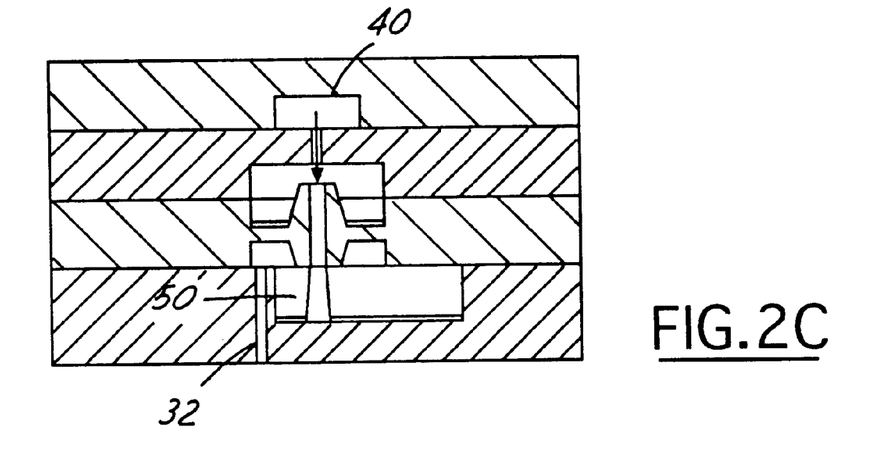

FIGS. 2A–2C illustrate the liquid dispensing device 90 formed in a substrate made of three layers of material, namely first layer 21, second layer 22 and third layer 23. The first layer 21 has gas pulse channels 40 and gas pulse feeders 41 leading into the second layer. The second layer 22 has reagent fill channels 12 leading into the structures in the third layer 23. The third layer 23 has metering capillaries 14 with inlets in communication with reagent fill channels 12 in the reagent distribution plate 22 and outlets.

The reagent fill channel 12 is preferably of dimensions that are large enough so that capillary forces do not inhibit draining of the reagent fill channel. Drainage can be enhanced by constructing a second layer 22 of a material that does not wet on contact with the liquids sought to be dispensed. Methods of forming thin, non-wetting coatings of perfluoroalkanes are described in Datta et al., U.S. Pat. No. 4,252,848. Alternatively, the surface energy of a surface of a reagent fill channel can be reduced by coating the surface with a silicone resin or a fluorine-containing resin, thereby reducing wetting. Such resins are described in Mochizuki et al., U.S. Pat. No. 5,652,079. The sides of the reagent fill channel 12 can also be rendered resistant to wetting, for instance, by reacting the surfaces with a reactive organo silane reagent such as SigmCote™, (Sigma Chemical Co., St. Louis, Mo.), dichlorooctamethylsiloxane ($C_2H_{24}Si_4O_3Cl_2$, Surfa-Sil™, Pierce Chemical, Rockford, Ill.) or modified organo silane such as an octadecyltrialkoxysilane (Aqua-Sil™, Pierce Chemical, Rockford, Ill.).

FIGS. 2A–2C also illustrate an assay plate 30, located below the capillary metering plate 23 with reaction wells 31 of the assay plate aligned with the outlets of the metering capillaries 14. The assay plate can be aligned with capillary metering plate such that the outlets of the metering capillaries open into the corresponding wells in the assay plate. The wells in the assay plate can be used, for example, to conduct assays, syntheses or other chemical processes. The assays may include, for example, tests for inhibitors, inducers or activators of chemical processes such as biological signal transduction reactions, or tests for the presence of a substance such as an immuno-assay, a hybridization assay, or a nucleic acid amplification assay.

The exemplified assay plate 30 can be reversibly and sealably attached to the third layer 23 to form a liquid tight seal, for instance by the use of the seals described in U.S. application Ser. No. 08/744,386, filed Nov. 7, 1996, now abandoned, (Dkt. No. 12385A) and U.S. application Ser. No. 08/630,018, filed Apr. 9, 1996 now U.S. Pat. No. 5,840,256 (Dkt. No. 12098). A gasket may be placed between third layer and the assay plate as described in U.S. application Ser. No. 08/556,036, filed May 31, 1995 (Dkt. No. 11402G) and U.S. Pat. No. 5,840,256 (application Ser. No. 08/630,018, filed Apr. 9, 1996, Dkt. No. 12098). (This latter patent is hereby incorporated by reference in its entirety.) In the illustration, vents 32 are formed adjacent to reactions wells 31. The vents 32 prevent back pressure from interfering in the dispensing of liquids.

Illustrated in FIGS. 2A–2C is the operation of the liquid dispensing device 90A. In FIG. 2A, the reagent fill channel 12 has been filled with liquid, resulting in metering capillaries 14 also being filled. Liquid flow into the reagent fill channel 12 is then curtailed and liquid is drained from the reagent fill channel 12, for example by capillary flow or through the use of gas pressure, so long as the pressure is less than that effective to eject liquid from the metering capillaries. The draining of the reagent fill channel 12 leaves the metering capillaries 14 filled with liquid, as illustrated in FIG. 2B. A pulse of gas can be applied to a gas pulse channel 40 (a portion of which is shown) with sufficient pressure to inject gas, by way of gas pulse feeder 41, into reagant fill channel 12 to cause the metered fluid 50 in the metering capillaries 14 to be ejected into the corresponding wells 31, as illustrated in FIG. 2C. If necessary, gas-flow through the excess fluid outlet 13 can be blocked to maintain the pressure causing fluid ejection from the metering capillaries 14. However, the gas outlet pathways can be sufficiently constricted to allow the formation of sufficient pressure. The dimensions of the metering capillaries 14 and the locations of gas pulse 41 feeders are selected so that the ejection of liquid from a subset does not sufficiently relieve the gas pressure to prematurely end the liquid ejection process.

In one embodiment, the structures housing the metering capillaries 14 as illustrated in FIGS. 2A–2C can protrude into the reagent fill channel 12 and away from the bulk of the flat surfaces of the lower surface of third layer 23 forming upper mesas 15 and lower mesas 16. The upper mesas 15 of the metering capillaries 14 protrude into the reagent fill channel 12 and thereby minimize the amounts of residual liquid in the reagent fill channel that can be inadvertently ejected by gas pressure. The lower mesas 16 minimize the amount of fluid diverted to flow along the bottom surface of the third layer 23. The upper and lower mesas as shown in the illustration are labeled "upper" and "lower" only for a matter of convenience. In some embodiments, mesas can be designed to have differing orientations.

Figure 3A:
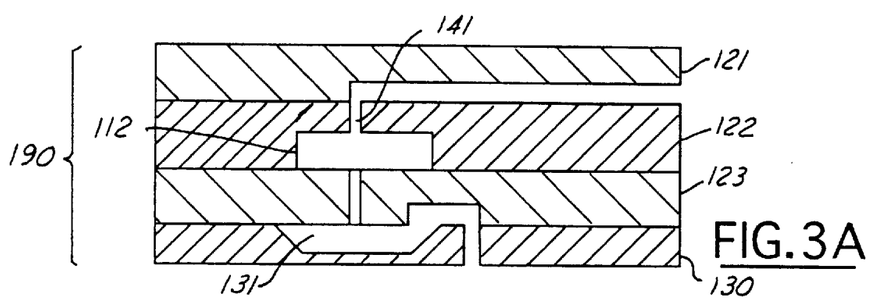
FIGS. 3A, 3B and 3C show the dispensing device as in FIG. 2 but without mesas at the top or bottom of metering capillaries.
Figure 3B:
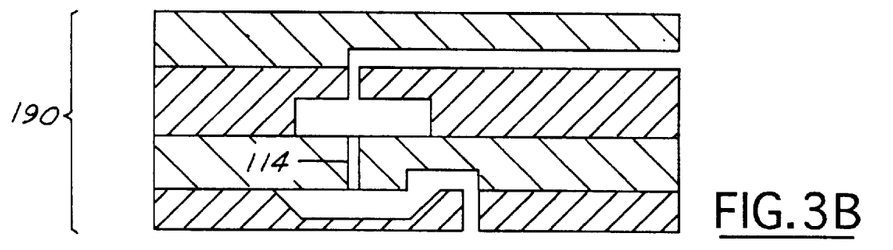
Figure 3C:
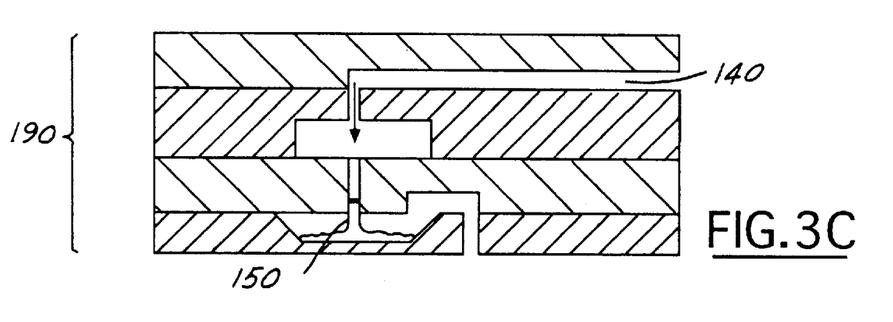

In another embodiment illustrated in FIGS. 3A–3C, a liquid dispensing device 190 also has the first layer 121, second layer 122 and third layer 123 like that of the liquid dispensing device 90A shown in FIGS. 2A–2C. The three layers of the liquid dispensing device 190 also have their component structures as in FIGS. 2A–2C such as gas pulse channel 140, gas pulse feeder 141, reagent fill channel 112, metering capillaries 114. Assay plate 130 with reaction wells 131 can be reversibly attached to the liquid dispensing device. However, the third layer ("capillary metering plate") 123 housing the metering capillaries 114 illustrated in FIGS. 3A–3C does not form mesas. The three panels, 3A, 3B and 3C illustrate a dispensing liquid 150.

In some embodiments, the surface areas surrounding the inlets and outlets of metering capillaries (e.g., 14 or 114) are not susceptible to wetting. For example, these areas can be treated with a reagent that modifies the surface wetting properties of the surface material.

Figure 4:
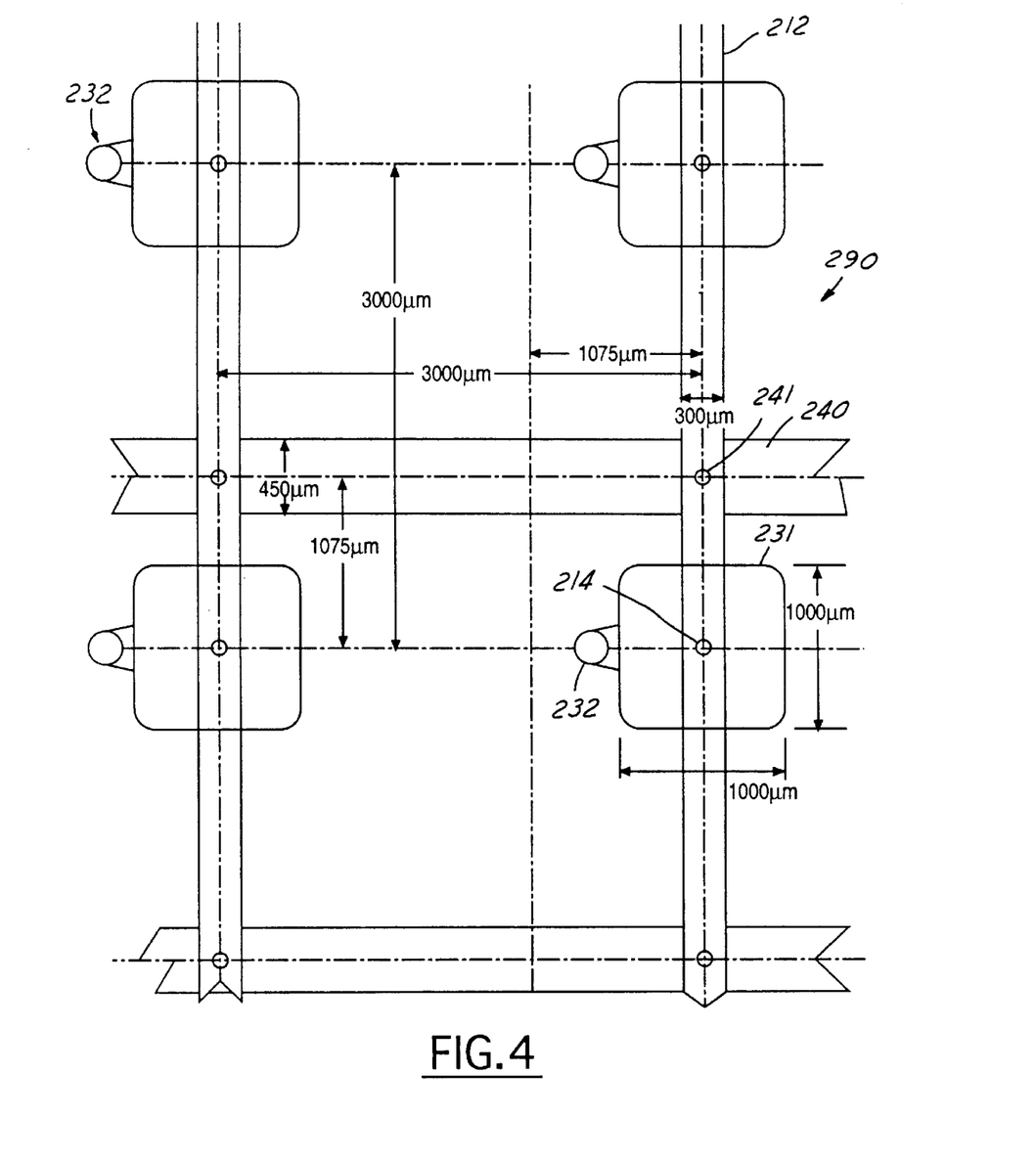
FIG. 4 shows a structural representation of the interior of a liquid dispensing device when viewed from below.
Figure 5:
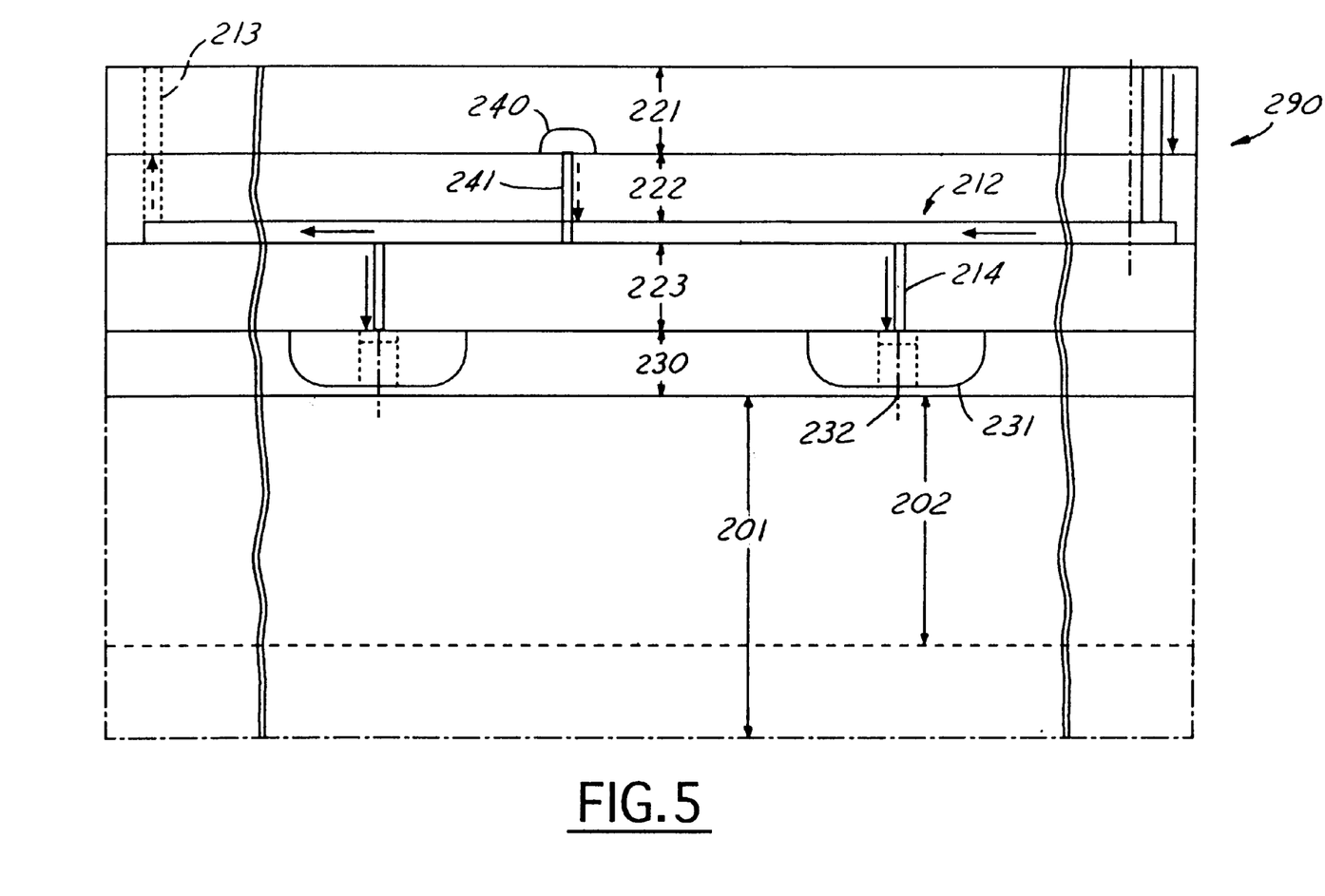
FIG. 5 shows a structural representation of the interior of the liquid dispensing device of FIG. 4 when viewed from a side of the long axis of a reagent fill channel, as indicated in FIG. 4.
Figure 6:
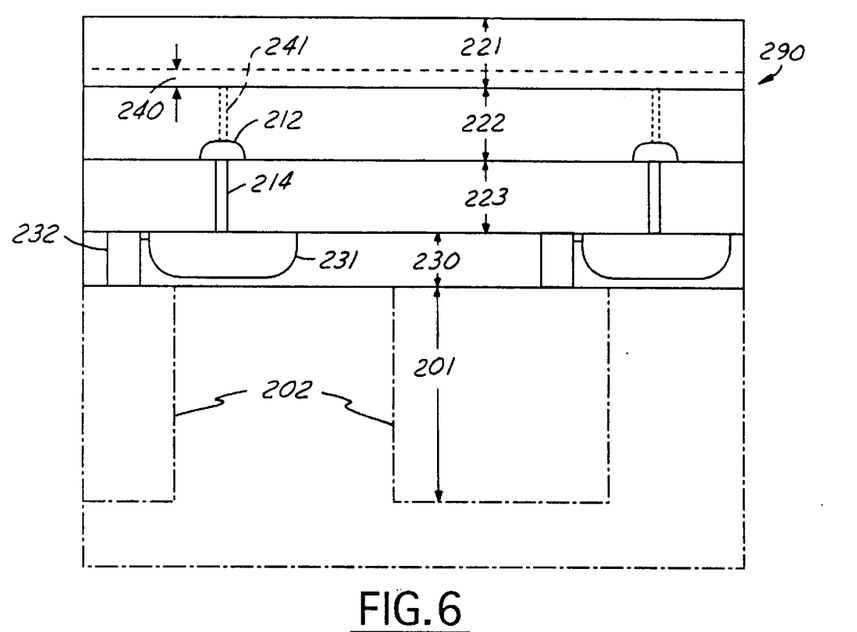
FIG. 6 shows a structural representation of the interior of the liquid dispensing device of FIG. 4 when viewed from a side of the long axis of the gas pulse channel, as indicated in FIG. 4.

FIGS. 4–6 represent schematic drawings of a liquid dispensing device 290 with assay plate attached as viewed from different angles to show relative positions of various structures and their relationship to each other. FIG. 4 is a schematic drawing of the liquid dispensing device with assay plate attached when viewed from the bottom. FIG. 5 is a schematic drawing of the liquid dispensing device 290 with assay plate 230 mounted on a fixture platen 201, where the liquid dispensing device 290 is viewed from the side of the long axis of the reagent fill channel 212. FIG. 6 is a schematic drawing of the liquid dispensing device with assay plate 230 mounted on a fixture platen 201 when the liquid dispensing device 290 is viewed from the side of the long axis of the gas pulse channel 240. FIGS. 5 and 6 also show the three layers, the first layer 221, second layer 222, and third layer 223 of the liquid dispensing device 290. In one embodiment, gas pulse channels 240 are arranged at right angles to the reagent fill channels 212. Gas pulse feeders 241 connect the gas pulse channels 240 and the reagent fill channels 212 to deliver gas into the latter.

Each well 231 in the assay plate has a vent 232 as can be seen in FIG. 6 to serve as an outlet for excess gas or liquid during operation of the liquid dispensing device or to provide an outlet for solutions during rinsing process. The fixture platen 201 on which the liquid dispensing device 290 with the assay plate 230 is mounted can have vent slots for venting fluids from the vents 232.

In the illustrated embodiment, reagent fill channel 212 has one or more reagent feed inlets 211 and one or more excess fluid outlets 213 (shown in FIG. 5). The excess fluid outlets 213 can be adapted to be connected to a vacuum source to evacuate liquid in the liquid dispensing device 290. For example, the liquid evacuation channels 213 connected to a vacuum source can be used to rapidly and evenly dry the liquid dispensing device 290 after each operation or rinsing of the liquid dispensing device. In the illustration, the gas pulse channels 240 are arrayed above the reagent fill channels 212, but this like other illustrated features is not a requirement; other design choices will be apparent to those of ordinary skill having benefit of this disclosure.

FIGS. 4 and 5 also include dimensions used in one embodiment However, the dimensions and relative positions can be varied so as to adapt to a given dispensing system and receiving substrate. In this embodiment, the dimensions of each gas pulse channel 240 in the first layer 221 are 450 $\mu$m wide by 150 $\mu$m deep. Similarly the reagent fill channels 212 in the second layer 222 are 300 $\mu$m wide by 100 $\mu$m deep. The metering capillaries 214 in the third layer 223 have a uniform length of 2.0 mm and a uniform diameter of 270 $\mu$m (which is, for example, 2 mm in length). The diameter of the gas pulse feeder 241 is 25 $\mu$m. In preferred embodiments, the size of this gas pulse feeder 241 is selected to minimize liquid flow into the gas pulse channels 240. The size of the each of the reaction wells 231 in the assay plate 230 is 1 mm by 1 mm by 0.3 mm, and pitch between wells is 1.5 mm. Another illustrative embodiment has 1.5 mm by 1.5 mm by 0.3 mm reaction wells. In some embodiments, the size of the reaction wells is selected to allow collection of all effluent from a cleavage step conducted in reaction cells of a liquid distribution system such as is described in U.S. Pat. No. 5,480,256 (Dkt. No. 11402G). Such cleavages preferably cleave a synthetic product from a solid support such as beads.

Figure 7:
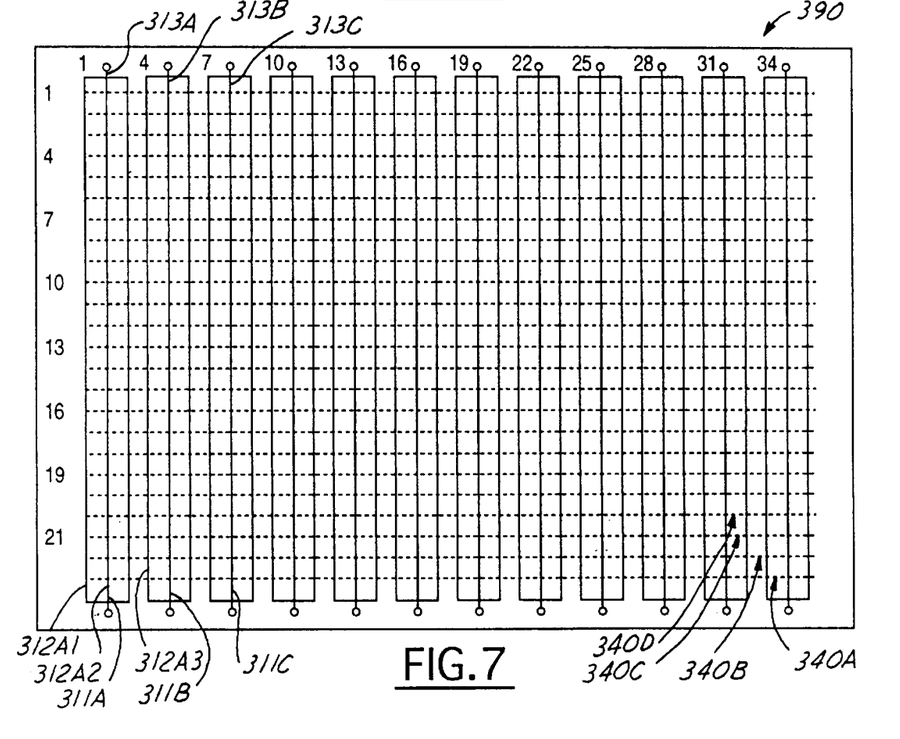
FIG. 7 shows a schematic top view of a liquid dispensing device for supplying reagents to a 864-well plate.

One aspect of the present invention is the use of an aliquoting apparatus having two or more liquid dispensing devices each with a specific capacity (i.e., volume dispensed per ejection into a well) liquid dispensing system and one or more receiving substrates. In one embodiment, for example, a first liquid dispensing device 390 has numerous reagent fill channels 312 (solid lines) and gas pulse channels 340 (dotted lines) designed to dispense into 864 wells as shown in FIG. 7. First gas pulse channel 340A, second gas pulse channel 340B, third gas pulse channel 340C, and fourth gas pulse channel 340D are specifically identified in the Figure. First alpha reagent fill channel 312A1, second alpha reagent fill channel 312A2 and third alpha reagent fill channel 312A3 are also specifically identified. Each such set of three reagent fill channels 312 is fed by a reagent fill inlet 311, such as first reagent fill inlet 311A, second reagent fill inlet 311B, and third reagent fill inlet 311C. The same triplets of reagent fill channels 312 are evacuated by excess fluid outlets 313, such as first excess fluid outlet 313A, second excess fluid outlet 313B, and third excess fluid outlet 313C. Note that the excess fluid outlets can flow upwards, instead of downwards as illustrated earlier, since negative pressure or a capillary flow system can be used to draw the excess liquid out of the reagent fill channels. In this embodiment, for example, the pitch between wells can be for example about 3 mm, such that the illustrated liquid dispensing system dispenses liquid to about 864 wells in an assay plate located on 4.5 inch by 3 inch substrate.

Figure 8:
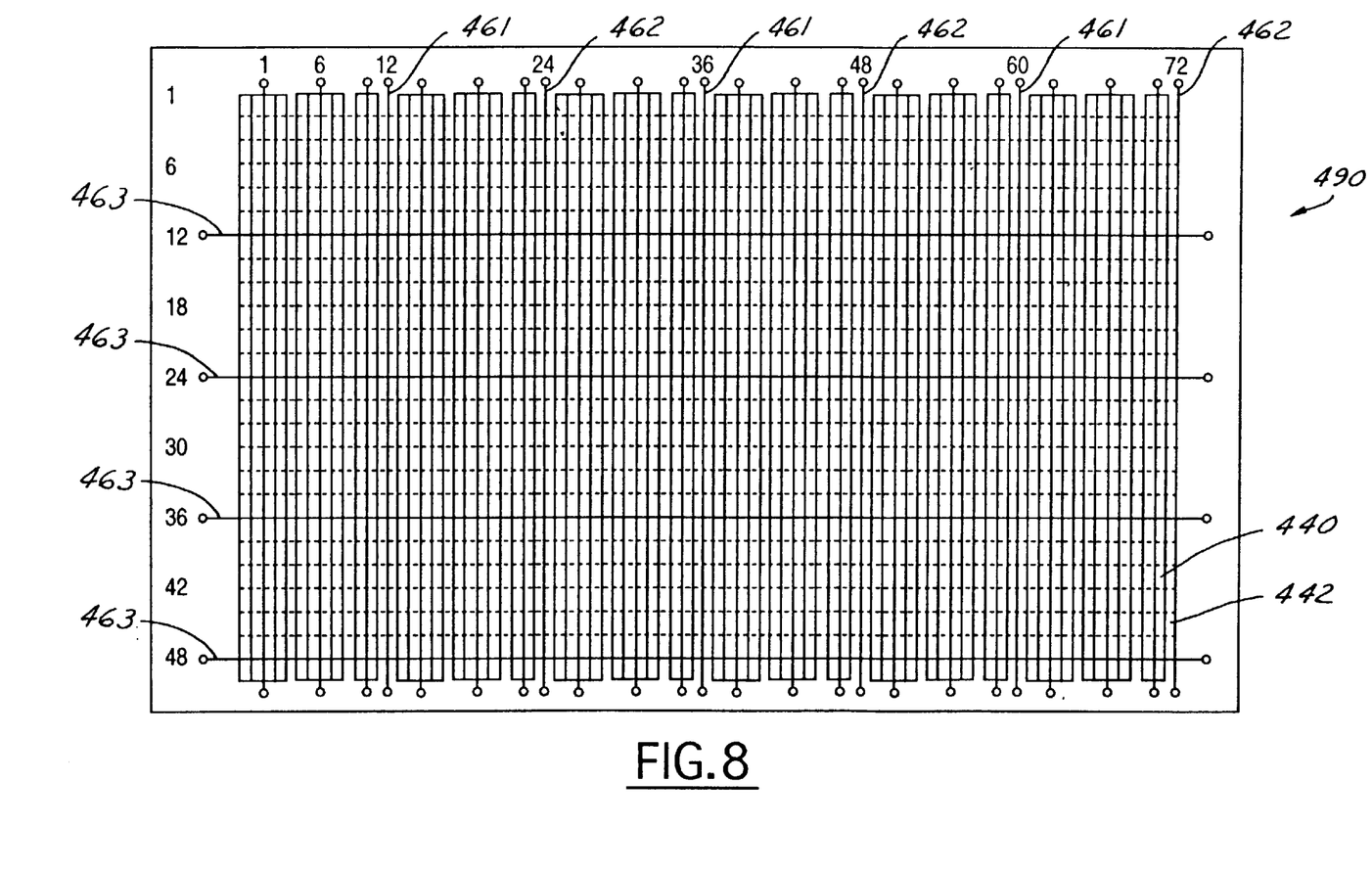
FIG. 8 shows a schematic top view of a liquid dispensing device for supplying reagents to a 3456-well plate.

In another embodiment, for example, a second liquid dispensing device 490 has numerous reagent fill channels 412 (solid lines) and gas pulse channels 440 (dotted lines) designed to dispense into 3456 wells as shown in FIG. 8. In this embodiment, for example, the pitch between wells is for example 1.5 mm, such that the illustrated liquid dispensing system dispenses liquid to about 3456 wells in an assay plate located on a 4.5 inch by 3 inch substrate. The illustrated liquid dispensing device 490 has first control reagent fill channels 461, second control reagent fill channels 462, and third control reagent fill channels 463, along with the more numerous sample reagent fill channels 412 and gas pulse channels 440. The control wells into which the control reagents are injected can be used to conduct different reaction controls, for instance, controls without test sample. For example, in an enzyme assay testing inhibitory effect of potential inhibitors on the enzyme, the first control reagent fill channels may dispense liquids with no test sample but with all other assay reagents including the enzyme, the second control reagent fill channels may dispense no test sample but with all other assay reagents plus a known inhibitor, and the third control reagent fill channel may dispense no test sample and no enzyme but with all other assay reagents. The sample reagent fill channels can be used to dispense liquids with all the ingredients such as the test sample, the enzyme, the inhibitor and all other assay reagents required to test for inhibition of the activity.

In another aspect, gas is delivered to gas pulse channels of the liquid dispensing devices 390 and 490 in a sequential fashion starting with the first gas pulse channel and then the second gas pulse channel, and so on, which results in gas pressure being sequentially received at a reagent fill channel at a first gas pulse feeder, a second gas pulse feeder, a third gas pulse feeder, etc. This sequential fashion can be termed "linearly" pressurizing segments of a reagent fill channel. Linear pressurization can proceed in one or both directions from a starting point in a reagent fill channel. In the liquid dispensing device 390, for example, gas pressure is sequentially delivered to a first gas pulse channel 340A, then a second gas pulse channel 340B, a third gas pulse channel 340C, and so on.

To control the delivery of gas an electronic controller such as an electrical processor can be used, for example in connection with electromechanical devices like switches, solenoids and the like. Remotely operated electromechanical devices can be used to open and close valves connected to the gas sources.

In FIG. 8, the liquid dispensing device 490 has gas pulse channels at two levels in the substrate so that gas can be delivered to sample reagent fill channels 412 and first and second control reagent fill channels 461 and 462 through gas pulse channels 440 (shown as dotted lines) formed in one level of the first layer while gas can be delivered to the perpendicularly oriented third control reagent fill channels 463 through gas pulse channels formed in a second level of the first layer.

Figure 9:
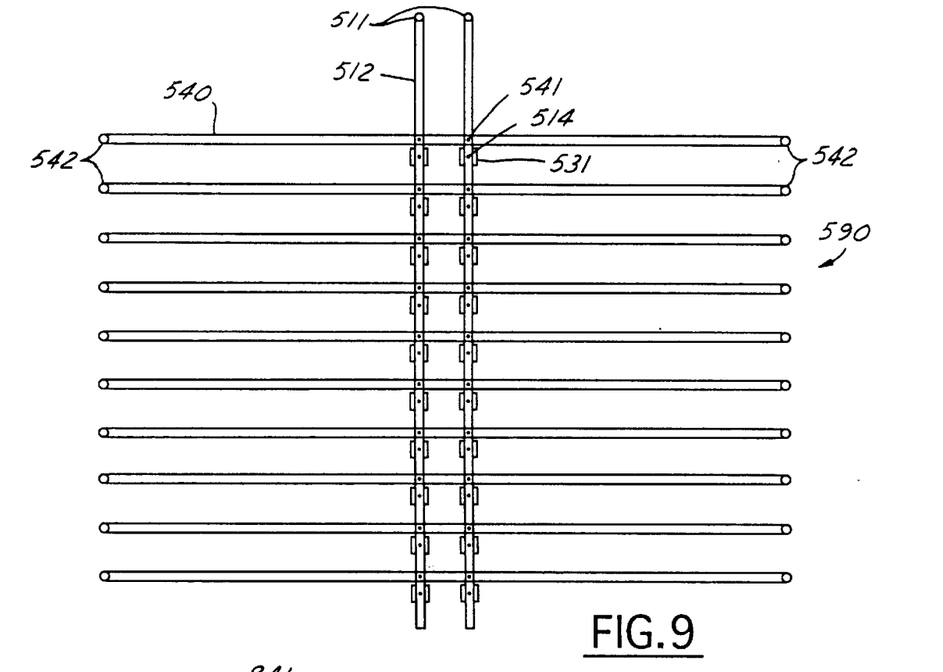
FIG. 9 shows an example of a liquid dispensing device.

The liquid dispensing device 590 of FIG. 9 is described below in Example 1.

Figure 10:
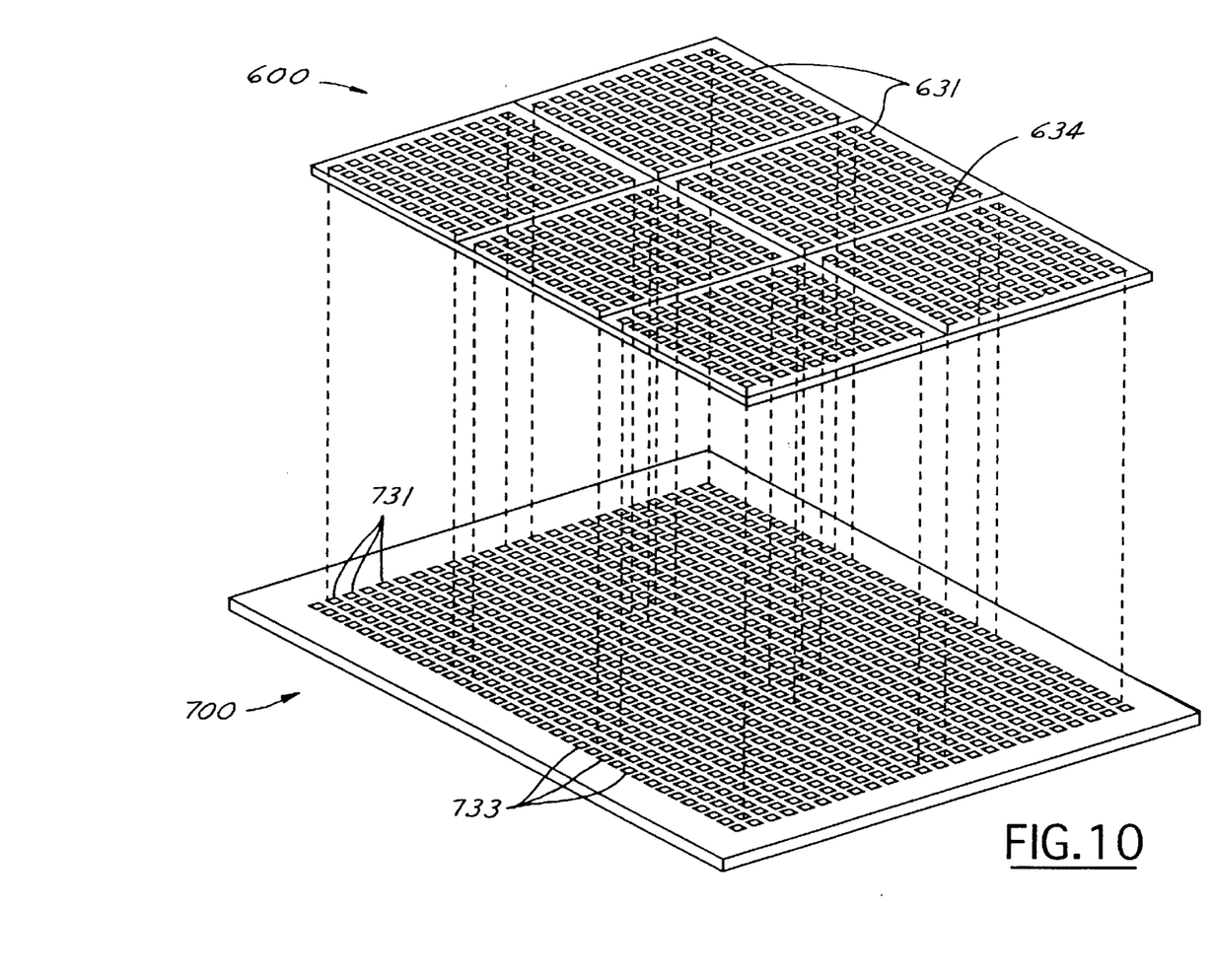
FIG. 10 shows a schematic diagram of assay plate to show the location of control wells and reaction wells, and the relation of the assay plate to a synthesis plate on which compounds can be synthesized by a combinatorial process.

For illustrative purposes, FIG. 10 shows two kinds of receiving substrates such as reaction plate composite 600 and assay plate 700. Reaction plate composite is made up of six reaction plates 601. Reaction plate composite 600 has evenly sectored reaction wells 631, the sectors separated by junction seams 634. Likewise, the assay plate 700 also has evenly sectored reaction wells 731. The reaction wells of the assay plate 700 map directly with the reaction wells of the reaction plate composite 600 but the portions of assay plate 700 that would map to the junction seams 634 of the reaction plate composite 600 are instead filled with control wells 733.

For example, the reaction plate composite 600 can be the plate composite on which a combinatorial array of test compounds was synthesized, for example, using the liquid distribution systems of U.S. Pat. No. 5,846,396 (application Ser. No. 08/556,036 filed May 31, 1995, Dkt. No. 11402G) or application Ser. No. 08/744,386, filed Nov. 9, 1996, now abandoned, (Dkt. No. 12385A). Or, the reaction plate composite 600 can be a replica plate matching the product outputs of a combinational synthesis. The junction seams 634 match, for example, the areas of a preferred liquid distribution system that are used for ancillary functions such as gas or liquid feed lines. This extra space can be taken advantage of to disperse control wells within the assay plate 700.

In an enzyme assay, for example, the different types of reagents that are required, in the assay plate 700 wells to conduct the assay, can be added from a single first liquid dispensing device. Or, the assay plate 700 can be transported, by hand or by means of a motorized transfer device such as a robot, to a second liquid dispensing device to add different reagents.

In one embodiment, a first liquid dispensing device 390 with the dispensing system illustrated in FIG. 7 is used to dispense solvents such as DMSO (Dimethylsulfoxide) into an alpha assay plate of 864 wells to dissolve chemicals (such as the products of a combinatorial process) used in an assay with the chemicals or reagents of the 864 wells dissolved. Pin devices such as the Biomek High Density Replicating Tool sold by Beckman Instruments, Fullerton, Calif. can be used to copy the 864 wells onto ¼th of the wells in a beta assay plate having 3456 wells (situated with ½ the cell pitch used with the alpha plate). Reagents from three additional alpha assay plates can be used to load unique reagents into the rest of ¾ of the wells of the beta assay plate. The beta assay plate can be transferred to a second dispensing device 490 with sample and control reagent fill channels as illustrated in FIG. 8 for further dispensing as required to complete an assay with different controls.

Given the small volumes involved, in some embodiments care is taken to assure mixing of separate fluids added to a well. For example, a plate 490 can be subjected to ultrasonic vibration to assure mixing.

Figure 11:
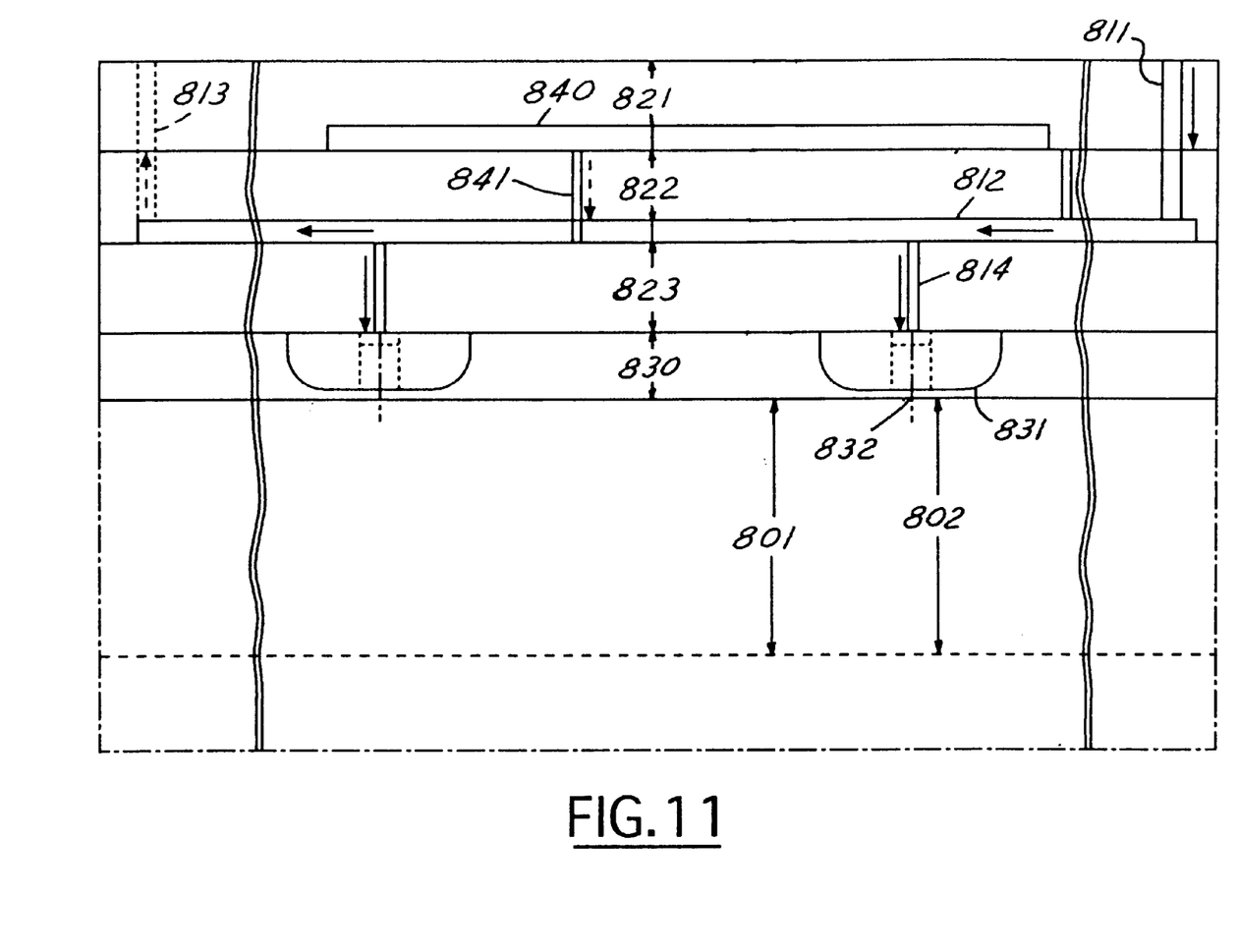
FIG. 11 shows a structural representation of the interior of a liquid dispensing device when viewed from a side of the long axis of a gas pulse channel and a reagent fill channel of the liquid dispensing device.
Figure 12:
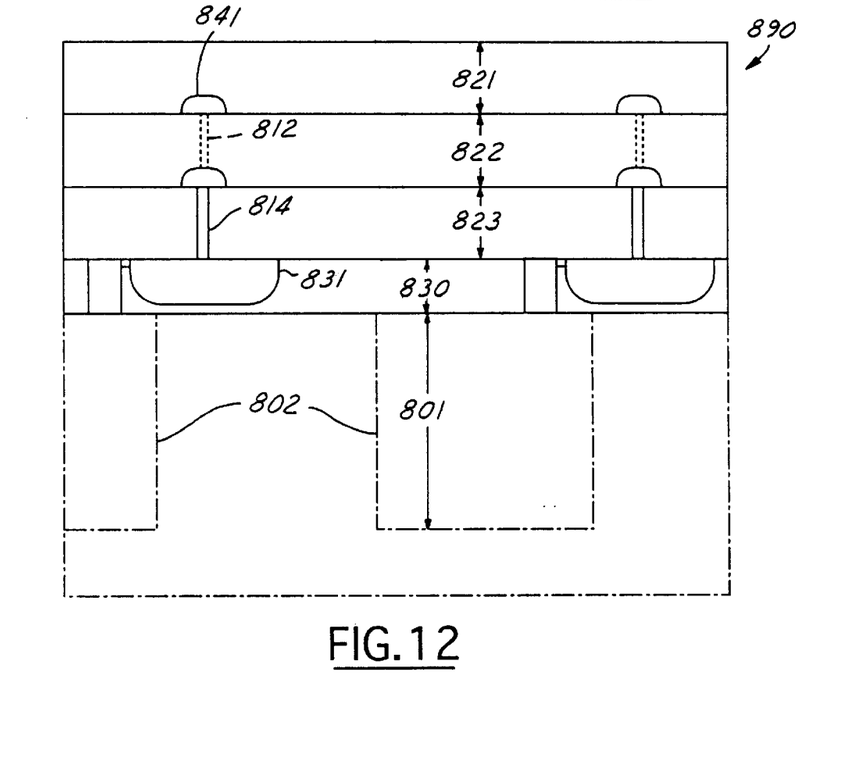
FIG. 12 shows a structural representation of the interior of the liquid dispensing device of FIG. 11 when viewed from a side looking into the the gas pulse channel and the reagent fill channel of the liquid dispensing device.

Another liquid dispensing device 890 (FIGS. 11 and 12) is similar to that of the liquid dispensing device 290 described above. The liquid dispensing device 890 also has the first layer 821, second layer 822 and third layer 823. The three layers of the liquid dispensing device also have their component structures such as gas pulse feeders 841 connecting the gas pulse channels 840 and the reagent fill channels 812, reagent feed inlets 811, excess fluid outlets 813, and metering capillaries 214. The component structures of assay plate 830 include one or more wells 831, and each well in turn having a vent 832. These features, further including fixture platen 801, function analogously to those described in FIGS. 4–6, except that the gas pulse channels 840 and reagent fill channels 812 are aligned in parallel.

The embodiment in which the gas pulse channels are parallel to the reagent fill channels is particularly preferred when one wishes to dispense in sequential rows from the metering capillaries. The gas pulse channels are located directly above (or below) the reagent fill channels. When a pulse of gas is introduced into one of the gas pulse channels, dispensing occurs in an entire row of metering capillaries. By sequentially stepping the pulsed gas from one row to another the assay plate receives the reagent in a row-scan fashion until the plate is entirely addressed. This embodiment is desirable for the following reasons: (1) it can reduce the complexity of the off-chip reagent supply system, (2) it can reduce the complexity of the detection system, especially for instrumentation for kinetic assays.

In operation, a device of the invention can, for example, deliver a 8 nL volume (with a metering capillary channel of diameter=100 $\mu$m and length=1.0 mm), a 46 nL volume (with a metering capillary channel of diameter=200 $\mu$m and length=1.5 mm), or a 42 nL volume (with example a metering capillary channel of diameter=300 $\mu$m and length= 2.0 mm) to multiple sites. In the case of the first example of a 8 nL metering channel, it is anticipated that a feed volume of about 200 $\mu$L to about 300 $\mu$L can be used to deliver this volume to each of 3,456 wells. The depth of each well is, in one preferred embodiment, no greater than 300 $\mu$m (and holds, for example, a 300 nL volume). Where appropriate to the application, liquid flowing through the excess fluid outlet can be recycled.

It will be recognized that the liquid dispensing device can be manufactured to adapt to the viscosity, capillary flow and other physico-chemical properties of a class of liquids, such as aqueous solutions or non-aqueous solutions. For example, a particular design might be appropriate for dispensing aqueous solutions and ethanol solutions, while another design taking into account the low viscosity and surface tension of the distribution channels can be used for dispensing other organic solutions.

Materials to fabricate the liquid dispensing device can be chosen from group resistant to the chemicals used for distribution and assaying. A preferred material is amenable to micro-fabrication, etching and replication (for example molding plastic replica plates). The layers of the liquid dispensing device are, for example, formed of a material that can be chemically etched, reactive ion etched, laser drilled or replicated from molds or tools made from these processes to form the needed structures, such as glass, quartz, silicon, doped silicon, or polymers in the case of replication. The replicated layers are formed of a moldable plastic such as polypropylene, polystyrene or Teflon™ (tetrafluoroethylene polymer). Preferred materials used for assay plates can be plastics such as polypropylene or Teflon™. Preferably, the thickness of the plates or layers making up the device is from about 1.0 mm to about 6.0 mm, more preferably from about 1.5 mm to about 3.0 mm.

To fabricate a device of the invention in glass, channels can be formed along the boundaries of glass plates that are joined together. Channel fabrication can be accomplished by etching techniques such as for example by chemical or reactive ion etching or laser ablation. Channels formed through plates are preferably formed by laser ablation. Preferably, the major surfaces of glass plates are roughened prior to drilling such channels by laser ablation, and in particular it is preferred to roughen the side of the plate at which the outbreak will occur. The roughening helps limit the scope of any fracturing that occurs at the outbreak site. Following laser ablation, the rough surface can be ground and polished.

Where fine features are desired, highly accurate techniques such as dry chemical ion etching are preferred. Dry chemical etching is discussed, for example, in S. M. Sze, "Semiconductor Devices, Physics and Technology", John Wiley & Sons, New York, 1985, pp. 457–465. In one such technique, plasma-assisted etching, an electrical field can be used to direct the plasma etchant along a given axis, thereby increasing the crispness of the etch boundaries. Following the formation of such plate-traversing channels, the surfaces of the plates can be lapped and polished. When the plates are sufficiently smooth, they can be permanently joined to other plates of the liquid dispensing device, for example using the anodic bonding technique described in U.S. Pat. No. 5,747, 169 (application Ser. No. 08/745,766, filed Nov. 8, 1996, Dkt. No. 11865). (This patent is incorporated herein by reference in its entirety.) The anodic bonding technique can be used, for example to join plates of glass, glass and silicon (See U.S. Pat. No. 5,846,396, Dkt. No. 11402G).

To fabricate a device of the invention in plastic, molding tools are fabricated usually in silicon using the same processes above. The tools are made with reverse features to produce a molded replications that have appropriate features.

In a further aspect of the invention, the aliquoting apparatus with liquid dispensing devices is preferably provided with an alignment detection mechanism. The alignment detection mechanism preferably has alignment markers on the device and the receiving substrate such as an assay plate. The alignment markers are preferably formed along the margins of the lower surface of the liquid dispensing device and the upper surface of the assay plate. The alignment markers may be for example mechanical markers such as notches, mesas, ridges, furrows, pins or holes. Other alignment markers such as magnetic, electrical or optical markers may also be used. The different alignment markers can be used either singly or in combinations. Preferably, the alignment markers of the liquid dispensing devices are adapted to engage with corresponding markers on the assay plates such that several assay plates requiring the same reagents or different reagents to be dispensed can be aligned precisely with a liquid dispensing device in a sequential fashion or a single plate can be aligned precisely, first with a first device and then with a second device.

The alignment detection mechanism further has an alignment detection device for determining the relative positions of the alignment markers of the liquid dispensing devices with respect to that of the assay plates. The alignment detection device preferably produces alignment data and transfers the alignment data to a controller. Preferably, the controller can be operated not only to transfer the assay plates between the liquid dispensing devises but also to adjust the alignment of the markers of the assay plates with the corresponding markers of a liquid dispensing device after receiving the data from the alignment detection device The present invention is further supported by the following non-limiting examples.

EXAMPLE 1
Fabrication of a liquid dispensing device

The liquid dispensing device 590 as shown in FIG. 9 is fabricated as follows. A first heat-resistant borosilicate glass plate (such as Pyrex™ glass) (3.5 inch by 5.0 inch by 30 mil) is etched to form on its bottom surface 10 parallel gas pulse channels 540 (450 $\mu$m wide by 150 $\mu$deep). All etchings of the first glass plate are conducted with chemicals. A second heat-resistant borosilicate glass plate (3.5 inch by 5.0 inch by 30 mil) is etched on its bottom surface to form two parallel reagent fill channels 512 (300 $\mu$m wide by 100 $\mu$m deep). At the ends of each reagent fill channel, reagent feed inlets 511 (300 $\mu$m diameter) are etched. The second plate is designed to be oriented above the first plate. Gas pulse inlets 542 (300 $\mu$m diameter) and gas pulse feeders 541 (25 $\mu$m diameter) are etched through the second plate. A silicon plate (3.5 inch by 5.0 inch by 40 mil) is reactive ion etched using an electric field to form crisp metering capillaries 514 (only the cross-sections are shown in the illustration) (the capillaries are 270 $\mu$m diameter by 1 mm long). The first glass plate, second glass plate and silicon plate were aligned as indicated in FIG. 9 and anodically bonded. To bond the two glass plates, a silicon layer (300 nm thick) is applied by evaporation under inert atmosphere (to prevent oxidation) to the under interface side of the second glass plate. The silicon-coated surface is then matched with the underside of the first glass plate, and the plates are anodically bonded. The silicon plate is directly anodically bonded to the second glass plate (i.e., without using a silicon coating). Shown in the drawing, for illustrative purposes, is an indication of the outlets of the metering capillaries aligned with reaction wells 531 (which are 1 mm by 1 mm by 0.3 mm deep) of an assay plate. In another example, the plate-traversing holes arc laser drilled.

EXAMPLE 2
Formation of Mesas

Figure 13A:
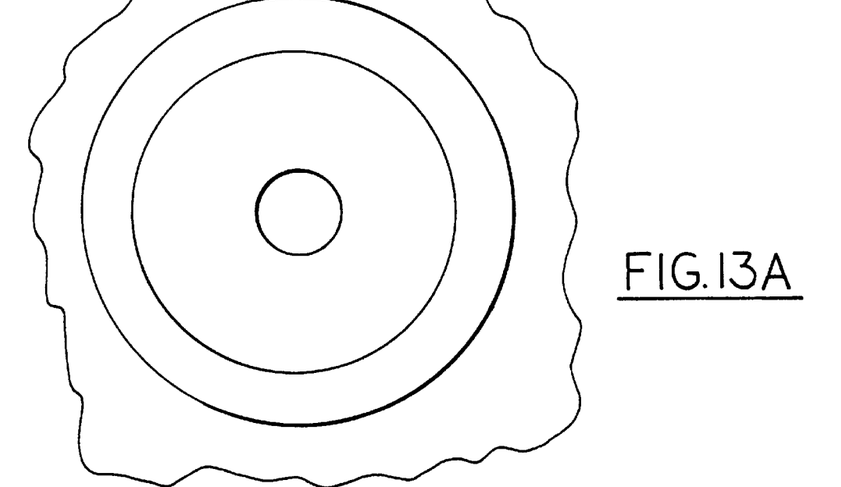
FIG. 13A shows a top view of a mesa having an outlet of a metering channel.
Figure 13B:
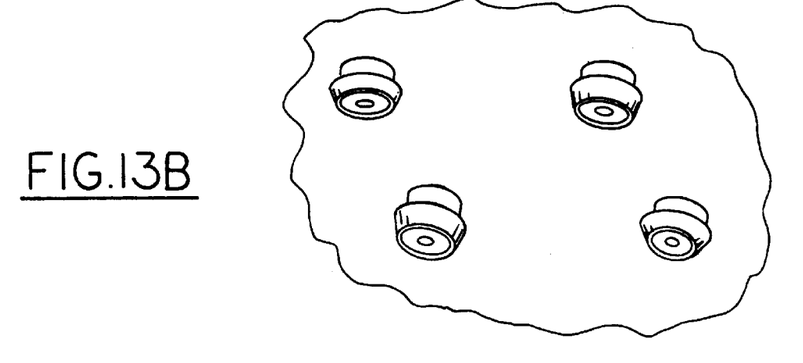
FIG. 13B shows an oblique view of four such mesas.
Figure 13C:
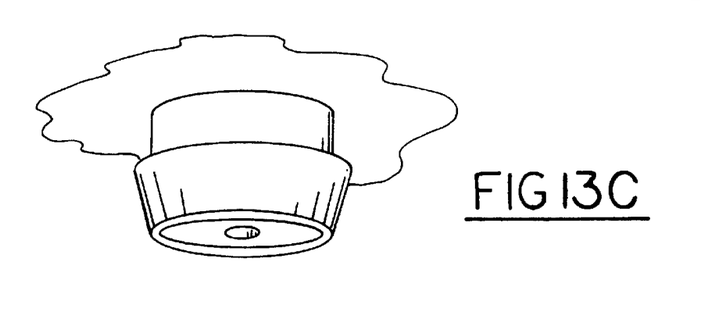
FIG. 13C shows a side view of such a mesa.

Metering cappilaries and mesas were formed on and in a silicon plate (3.5 inch by 5.0 inch by 40 mil) by reactive ion etching using an electric field. FIG. 13A shows a photograph of a top view of a 600 $\mu$m wide by 200 $\mu$m high mesa in which a 75 $\mu$m wide hole has been laser drilled. FIG. 13B shows an oblique view of four of the mesas shown in FIG. 13A. FIG. 13C shows a side view of one of the mesas. Photolithography techniques were used to create 600 $\mu$m wide areas covered by a mask (which was a photoresist layer) centered at the anticipated location of the mesas. An electric field was used to direct the etchant, directly down on the silicon plate. This reactive ion technique assured that only a minimal amount of lateral etching occurred. Holes were laser drilled through the tops of the mesas. The resulting mesas are those pictured in FIGS. 13A–13C.

While this invention has been described with an emphasis upon preferred embodiments, it will be obvious to those of ordinary skill in the art that variations in the preferred devices and methods may be used and that it is intended that the invention may be practiced otherwise than as specifically described above.

What is claimed:

1. A liquid dispensing device for delivering defined volumes of a liquid comprising:
   (a) a reagent fill channel of first cross-sectional dimensions;
   (b) one or more metering capillaries of second cross-sectional dimensions
      (i) connected to the reagent fill channel, and
      (ii) having an exit; and
   (c) one or more sources of gas connected to the reagent fill channel,
      wherein the first cross-sectional dimensions are such that after the one or more metering capillaries are filled from the reagent fill channel, the reagent fill channel is drained of liquid without applying a pressure effective to drain liquid in the one or more metering capillaries, and wherein the source of gas is adapted to apply pressure to eject the liquid in the metering capillaries; and wherein a metered amount of liquid is dispensed by said ejection.

2. The liquid dispensing device of claim 1, wherein a structure forming at least one of the metering capillaries forms a mesa into the reagent fill channel, or a mesa at the exit, or forms mesas into the reagent fill channel and at the exit.

3. The liquid dispensing device of claim 1, comprising two or more said reagent fill channels connected to one or more metering capillaries, wherein the liquid dispensing device is adapted to dispense via separate reagent fill channels two or more different reagents.

4. The liquid dispensing device of claim 1, further comprising two or more connections of the reagent fill channel to one or more gas sources.

5. The liquid dispensing device of claim 4, wherein two or more of the connections arc to separate gas sources.

6. The liquid dispensing device of claim 5, further comprising a controller for sequentially activating the gas sources to sequentially and linearly pressurize segments of the reagent fill channel.

7. An aliquoting apparatus comprising:
   (1) a first liquid dispensing device of claim 1 and a second liquid dispensing device; and
   (2) a motorized transfer device for moving a receiving substrate from the first liquid dispensing device to the second liquid dispensing device, wherein the receiving substrate receives liquids ejected from the first or second liquid dispensing devices.

8. The aliquoting apparatus of claim 7, wherein the first and second liquid dispensing devices comprise alignment markers, and the aliquoting apparatus is adapted to align and operate with receiving substrates having mechanical, magnetic, electrical or optical alignment markers.

9. The aliquoting apparatus of claim 8, wherein the first and second liquid dispensing devices comprise mechanical, magnetic, electrical or optical alignment markers.

10. The aliquoting apparatus of claim 8, further comprising:
   (3) an alignment detection device for determining the relationship between the alignment markers on either the first or second liquid dispensing system and the alignment markers on a receiving substrate and producing corresponding alignment data; and (4) a controller for receiving alignment data from the alignment detection device and operating the motorized transfer device to improve the alignment data.

11. A method of dispensing two or more liquids into two or more mixing sites on a receiving substrate comprising:
   (i) providing a first and a second liquid dispensing device of claim 1, with the receiving substrate aligned with the first liquid dispensing device;
   (ii) dispensing, from the first liquid dispensing device, a first liquid to the two or more mixing sites;
   (iii) moving the receiving substrate to align with the second liquid dispensing device; and
   (iv) dispensing, from the second liquid dispensing device, a second liquid to the two or more mixing sites.

12. A method of dispensing two or more liquids into two or more mixing sites on a receiving substrate comprising:
   (i) providing a liquid dispensing device of claim 1, with the receiving substrate aligned therewith;
   (ii) dispensing, from the liquid dispensing device, a first liquid to the two or more mixing sites;
   (iii) filling one or more reagent fill channels of the liquid distribution device with a second liquid; and
   (iv) dispensing from the liquid dispensing device the second liquid to the two or more mixing sites.

13. A liquid dispensing device for delivering defined volumes of a liquid comprising:
   (a) a reagent fill channel;
   (b) one or more metering capillaries
      (i) connected to the reagent fill channel, and
      (ii) having an exit, wherein a structure forming at least one of the metering capillaries forms a mesa into the reagent fill channel, or a mesa at the exit, or forms mesas into the reagent fill channel and at the exit; and
   (c) one or more sources of gas connected to the reagent channel, wherein after filling the one or more metering capillaries, the reagent fill channel is adapted to drain of liquid while liquid is retained in the one or more metering capillaries and wherein the source of gas is adapted to apply pressure to eject the liquid in the metering capillaries.

14. The liquid dispensing device of claim 13 wherein two or more metering capillaries are connected to the reagent fill channels.

15. The liquid dispensing device of claim 13, wherein the two or more metering capillary structures comprise mesas into the reagent fill channel.

16. The liquid dispensing device of claim 14 wherein the connections to sources of gas comprise two or more connections and further comprising:
   (d) a controller for sequentially activating the gas sources to sequentially pressurize segments of the reagent fill channel.

17. The liquid dispensing device of claim 1, further comprising
   (e) two layers of substrate annealed together, wherein the metering capillaries are formed through the bottom layer and the reagent fill channel is formed at the junction of the two lower layers.

18. The liquid dispensing device of claim 16, further comprising:
   (f) at least one additional layer of substrate annealed to said two layers of (e); and
   (g) one or more gas distribution channels formed at the junction of said additional layer and one other layer, wherein at least one gas distribution channel is connected to the reagent fill channel to provide the said connected gas source.

* * * * *